US005695445A

United States Patent [19]
Khouri

[11] Patent Number: 5,695,445
[45] Date of Patent: Dec. 9, 1997

[54] METHOD AND APPARATUS FOR SOFT TISSUE ENLARGEMENT

[76] Inventor: Roger K. Khouri, 2 Kingsbury Pl., St. Louis, Mo. 63112

[21] Appl. No.: 504,640

[22] Filed: Jul. 20, 1995

Related U.S. Application Data

[63] Continuation of Ser. No. 220,186, Mar. 30, 1994, Pat. No. 5,536,233.

[51] Int. Cl.$^6$ ...................................................... A61F 5/00
[52] U.S. Cl. ............................................... 600/38; 601/14
[58] Field of Search ................. 600/38–41; 128/897–98; 601/6–14

[56] References Cited

U.S. PATENT DOCUMENTS

| | | |
|---|---|---|
| 936,434 | 10/1909 | Eganhouse. |
| 1,312,619 | 8/1919 | D'Orsay. |
| 2,616,417 | 11/1952 | Holbrook. |
| 3,382,867 | 5/1968 | Reaves. |
| 3,631,853 | 1/1972 | Burdette, Jr. |
| 3,785,369 | 1/1974 | Tallent. |
| 3,874,387 | 4/1975 | Barbieri. |
| 4,834,110 | 5/1989 | Richard. |
| 4,856,498 | 8/1989 | Osbon. |
| 4,856,499 | 8/1989 | Kelly. |
| 5,234,401 | 8/1993 | Yamanaka. |

FOREIGN PATENT DOCUMENTS

WO 91/17727 11/1991 European Pat. Off.

OTHER PUBLICATIONS

Copy of *Enlargement Book*, ©1990 Topco Books.

Copy of *An Anthology Of Plastic Surgery*, edited by Harry Hayes, Jr., M.D., specifically Section 6 entitled "Quackery and Nostrums", Aspen Publishers, Inc., 1986, pp. 163–175.

Article entitled "The Tension–Stress Effect on the Genesis and Growth of Tissues—Part I. The Influence of Stability of Fixation and Soft–Tissue Preservation" by Gavriil A. Ilizarov, AM., M.D., Ph.D., from *Clinical Orthopaedics and Related Research*, from Section III, entitled Basic Science And Pathology, No. 238, Jan. 1989, pp. 249–281.

Article entitled "The 'Niplette': an instrument for the non-surgical correction of inverted nipples" by D.D. McGeorge, from *British Journal Of Plastic Surgery* 1994, pp. 46–49.

Copy of *How To Enlarge Your Penis*, ©1988 House One, expurgated version.

Brochure entitled "Nipple Enlargement System" by Joel Kaplan, Ph.D., 1993.

Article entitled "The Ilizarov Technique: A Method To Regenerate Bone And Soft Tissue" by Dror Paley, M.D., et al., pp. 1–41, published prior to Mar. of 1993.

Article entitled "The Callotasis Method of Limb Lengthening" by Roberto Aldegheri, M.D., et al., from *Clinical Orthopaedics and Related Research*, No. 241, Apr. 1989, pp. 137–145.

Article entitled "Histophathology of Human Expanded Tissue" by Krystyna A. Pasyk, M.D. et al., from *Clinics in Plastic Surgery*, vol. 14, No. 3, Jul. 1987, pp. 435–445.

Article entitled "The Expansion of an Area of Skin by Progressive Distention of a Subcutaneous Balloon—use of the Method for Securing Skin for Subtotal Reconstruction of the Ear", by Charles G. Neumann, M.D., from *Plastic And Reconstructive Surgery* Feb., 1957, pp. 124–130.

(List continued on next page.)

*Primary Examiner*—John P. Lacyk
*Attorney, Agent, or Firm*—Howell & Haferkamp L.C.

[57] ABSTRACT

An apparatus and method for enlargement of soft tissue such as breasts or a penis is comprised of a dome configured to fit over the area of desired augmentation. The dome has a rim with a surface area equal to or greater than the normal area of the dome opening to prevent medical complications caused by excessive pressure to the skin. The dome also includes a vacuum pump with a power source, pressure sensor, and servomechanism for regulating the pressure within the dome.

32 Claims, 2 Drawing Sheets

OTHER PUBLICATIONS

Article entitled "Tissue Expansion in Soft–Tissue Reconstruction" by Chedomir Radovan, M.D., from *Plastic and Reconstructive Surgery*, Oct. 1984, pp. 482–492.

Article entitled "Elongation of Peripheral Nerve and Viscera Containing Smooth Muscle" by Ernest K. Manders, M.D., et al., from *Clinics in Plastic Surgery*, vol. 14, No. 3, Jul. 1987, pp. 551–562.

Article entitled "Rapid Elongation of Arteries and Veins in Rats with a Tissue Expander" by G. Björn Stark, M.D., et al., from *Plastic and Reconstructive Surgery*, Oct. 1987, pp. 570–581.

METHOD AND APPARATUS FOR SOFT TISSUE ENLARGEMENT

This application is a Continuation of Ser. No. 08/220,186 Mar. 30, 1994 U.S. Pat. No. 5,536,233.

BACKGROUND AND SUMMARY OF THE INVENTION

There are numerous instances where persons desire enlargement of the soft tissues in their bodies. One such instance is for the replacement of one or both breasts amputated during a mastectomy in order to restore physiological symmetry and psychological well-being. Other instances are for correction of natural abnormalities such as dimpling. Still other instances are for augmentation of physical attributes to improve cosmetics and self-esteem. These latter soft tissue enlargements are principally directed to breast enlargement in females and penis enlargement in males.

Prosthetic implants have been developed for insertion below the skin. However, the severity of the potential complications including scarring, implant rupture, capsular contracture, necrosis and implant migration as well as the recent adverse publicity thereof have significantly reduced the desirability of these implants. Thus, there is a societal need for other means to obtain soft tissue enlargement.

Some soft tissue enlargements occur naturally. For instance, during pregnancy the skin over a woman's abdominal region enlarges approximately nine times its previous area to accommodate the fetus without a proportional decrease in skin thickness. In other words, the abdominal skin tissue actually enlarges and does not merely stretch during pregnancy. Similarly, the skin will expand to accommodate any growth under the skin.

In the past, plastic surgeons have used this phenomena to their advantage to expand skin in order to accommodate prosthetic implants. To conduct this procedure, the surgeon inserts a balloon beneath the skin in the area where additional skin is desired. By progressively expanding the balloon, the skin first stretches and eventually actually grows to accommodate the increased volume underneath it. When the desired amount of skin is formed, the balloon is deflated and removed, and the implant is inserted into the cavity left by the balloon. Similar methods have been used by African native tribes to enlarge lips, nostrils, and earlobes.

Other surgical techniques have used tissue expansion to achieve other types of soft tissue growth. For instance, balloons have been successfully expanded underneath nerves, veins, tendons, and the like to thereby elongate these tissues to repair damage and alleviate various abnormalities.

A more advanced surgical method is known as callotasis or limb lengthening. This method comprises cutting the bone about its periphery at the location where lengthening is desired, leaving the tissues inside and around the bone intact. Brackets are attached to the bone on each side of the separation, and the bone segments are slowly pulled away from one another while remaining integral over a period of several months. Not only does this cause the mended bone to be longer, but also the soft tissue surrounding the bone actually grows to accommodate the increased limb length. Similar methods have been used by African native tribes to lengthen necks for cosmetic purposes.

Each of these above-mentioned apparatuses and methods requires an invasive surgical technique to accomplish the soft tissue expansion. Invasive techniques increase the likelihood of the complications associated with the procedure including those mentioned above with respect to implant surgery. In addition, the expense of surgery precludes many persons having their abnormalities corrected or physical attributes enhanced.

Other soft tissue enlargement techniques have been developed which use other mechanisms to cause the enlargement. For instance, an instrument and technique have been developed for the non-surgical correction of inverted nipples due to short lactiferous ducts. The instrument is comprised of a cup having an internal volume shaped like that of the final desired nipple. The user places the cup over the inverted nipple, pumps the air out of the cup with a syringe and adjusts the vacuum within the cup using a check valve to just below the threshold of discomfort. Thus attached, the device puts the lactiferous ducts in tension and extends them sufficiently after two to three months of wear at 8–12 hours per day.

Although this device is sufficient for its intended purpose, it is not suitable for general soft tissue enlargement. Laceration and contusion can occur if too strong of a suction is applied to soft tissue. As the pressure within the inverted nipple instrument is not regulated, contusion or laceration can occur. When a vacuum is developed within the cup of the instrument, an equal and opposite force is applied to the patient about the rim of the cup. Excessive contact forces against the patient can cause ulceration, laceration, and contusions. As the contact forces are not regulated in the nipple instrument, these further complications also can occur. In addition, general soft tissue enlargement is not feasible with the instrument due to the size and shape of the cup.

Another prior art device is disclosed in U.S. Pat. No. 936,434 as a device for enlarging a woman's breasts. This device included a pair of cups for placement on the breasts and a pump for exhausting the air. However, this patent provides no teaching as to the pressures to be used, the potential danger to the skin tissues, or any suggestions as to how the device is to be retained in place during use. Apparently, the device is used in a clinical setting and is not suitable for long term wear such as for 8–10 hours. As the patent suggests that the vacuum acts to cause the veins and arteries to engorge, thereby nourishing the breasts, it is clear that the patentee is suggesting that the breast tissue actually expands through this expansion of blood vessels alone. This patent has been the subject of ridicule by at least one medical authority. See "An Anthology Of Plastic Surgery" edited by Harry Hayes, Jr., M.D., Section 6, "Quackery and Nostrums" pub. 1986 by Aspen Publishers, Rockville, Md.

Finally, another prior art device although notorious is worthy of note. This device is commonly referred to as a penis pump and is sold primarily as a novelty as its long-term enlargement efficacy has never been proven and is in fact universally disclaimed by its distributors. The device is comprised of a cylinder having one open end into which the penis is inserted and a pump attached to it such that a vacuum can be created within the cylinder. Not only does this device have the same drawbacks as the nipple instrument with respect to potential complications, but also it is unlikely that sufficient vacuum can be maintained by the device to cause any notable long-term soft tissue enlargement. Further, this device is apparently designed to accomplish two tasks unrelated to enlargement. First, the device is used for stimulation and sexual gratification. Second, the device is used to promote erection by drawing blood into the penis.

Most of these prior art devices and methods have failed to achieve long term soft tissue enlargement while preventing damage to the soft tissue being enlarged, as well as surrounding tissue. The inventor herein has succeeded in designing and developing a new generalized method and apparatus for soft tissue enlargement which prevents damage to soft tissue. The apparatus used for this enlargement is comprised of a rigid fluid-impervious dome having a rim about its periphery and a vacuum pump for reducing pressure within the dome. The rim has sufficient surface area such that the pressure applied to the patient by the rim is less than or equal to the negative pressure applied to the soft tissue under the dome. Thus, as long as pressure within the dome is regulated to a limit below which medical complications cannot occur, the opposing contact pressure against the patient is below this threshold as well. With this approach, damage is avoided not only to the soft tissue being enlarged, but the surrounding tissue as well. In the preferred embodiment of the apparatus, the vacuum pump has a self-contained power source. In addition, a pressure sensor and servomechanism control the pump such that the vacuum within the dome is maintained at a magnitude less than 35 mm Hg. Variant embodiments may be configured to fit over and enlarge a human breast, a human penis, or any other desired area.

The method of use is comprised of the steps of attaching the dome to the location of desired enlargement, and creating a vacuum within the dome. The vacuum should be maintained for a minimum of eight hours per day and results should be sufficient after several months.

While the practical advantages and features of the present invention and method have been briefly described above, a greater understanding of the novel and unique features of the invention may be obtained by referring to the drawings and Detailed Description of the Preferred Embodiment which follow.

DETAILED DESCRIPTION OF THE PREFERRED EMBODIMENT

Figure 1:
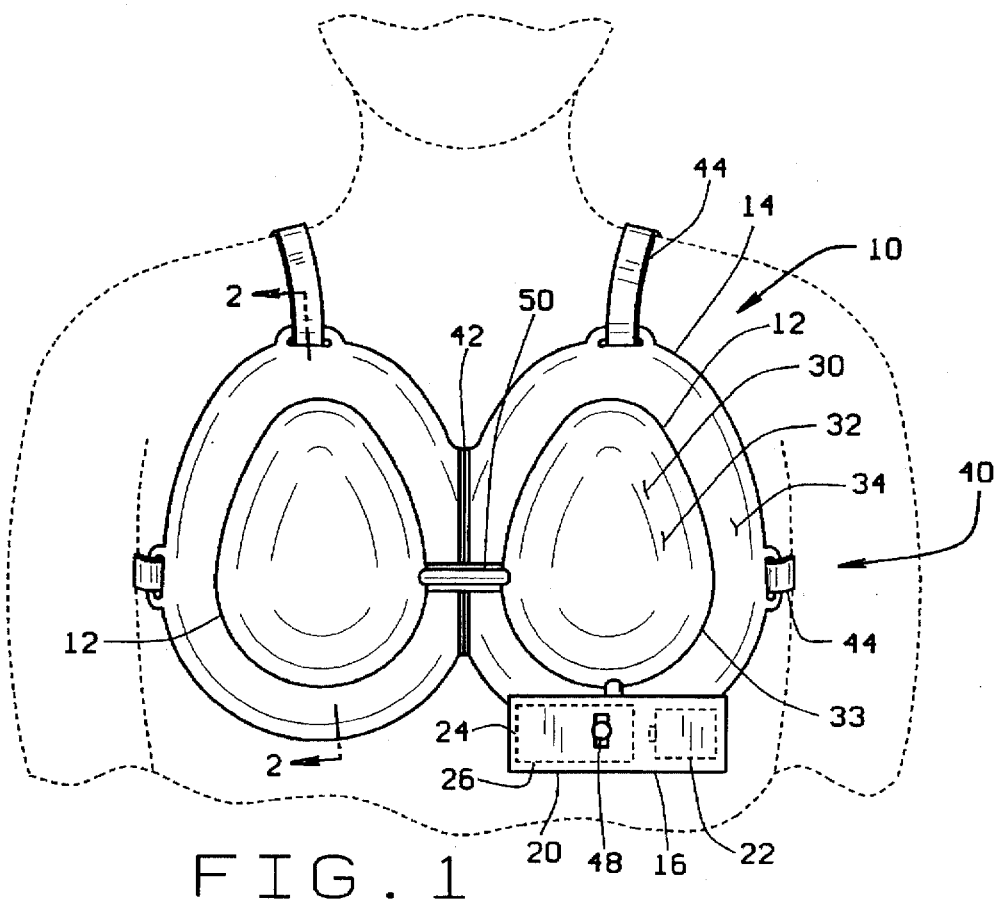
FIG. 1 is a front elevation view of the soft tissue enlargement apparatus of the present invention, showing the breast augmentation embodiment.

The soft tissue enlargement apparatus 10 is generally comprised of a dome 12 having a rim 14 and vacuum pump assembly 16 for creating a vacuum within the dome. Although the vacuum pump assembly 16 may be a separate hand-held pump in one variant embodiment, in the preferred embodiment the vacuum pump assembly 16 is a self-contained vacuum pump 20 with an independent power source 22, pressure sensor 24, and servomechanism 26 for driving, regulating and controlling the vacuum pump 20.

Regulation of the pressure within the dome is essential to prevent contusions caused by rupturing capillaries adjacent the surface of the skin. Medical data suggest that these contusions will not occur if pressure within the dome is maintained at less than 25–35 mm Hg. Thus, the vacuum pump 20 must be regulated to control the pressure within the dome to within this limit. In addition, skin ulceration can occur if excessive contact pressures are applied thereto. Medical data suggest that a contact pressure less than 15–20 mm Hg may be applied indefinitely without such ulceration. However, contusions may occur due to positive contact pressures upon the skin at pressures above this ulceration limit. The preferred embodiment of the present invention was developed with these limits in mind and will not apply a vacuum or a contact pressure greater than 25–35 mm Hg.

Figure 3:
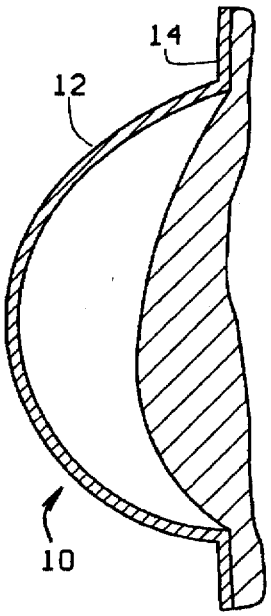
FIG. 3 is a cross-sectional schematic of a dome and soft tissue in the early stages of enlargement.
Figure 4:
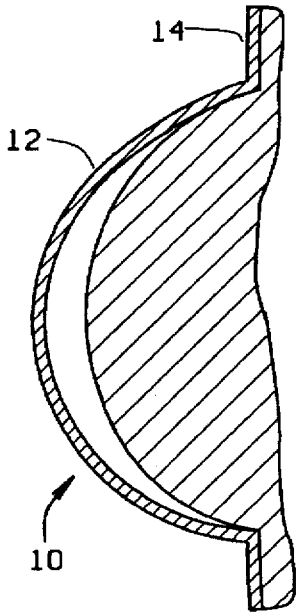
FIG. 4 is a cross-sectional schematic of a dome and soft tissue in the latter stages of enlargement.

Several forces are developed within the dome and about the rim as a result of evacuating air from the dome. A suction force is developed within the dome 12 equal to the vacuum pressure multiplied by the enclosed tissue surface area 30. The vector sum of the suction force upon the tissue surface area 30 may be called the normal force and is equal to the vacuum pressure multiplied by the normal area 32 of the dome opening, i.e., the area bounded by the periphery 33. An opposing force is imposed on the user by the rim 14 to balance the normal force and is equal but opposite to the normal force. The contact pressure of the rim 14 against the user is equal to this opposing force divided by the annular rim surface area 34, i.e., the surface area between the rim and patient which supports the dome's pressure. Therefore, if the rim surface area 34 is configured to be greater than or equal to the normal area 32 at the dome opening, then the contact pressure against the patient's skin will not exceed the magnitude of the vacuum pressure within the dome 12. Another physical phenomenon further aids in the enlargement forces upon the soft tissue under the dome 12. If the tissue only slightly protrudes into the dome as shown in FIG. 3 and as is typically the initial condition, then the surface area 30 under the dome is only slightly larger than the normal area 32 at the dome opening. Therefore, as the suction force is directly proportional to the surface area of the tissue under the dome, the suction force is only slightly larger than the normal force. As enlargement occurs, more tissue protrudes into the dome 12 as shown in FIG. 4 thereby providing more surface area 30 under the dome. Because the surface area 30 under the dome is larger, the suction force generated is increased. Thus, the rate of enlargement increases as treatment continues.

Figure 2:
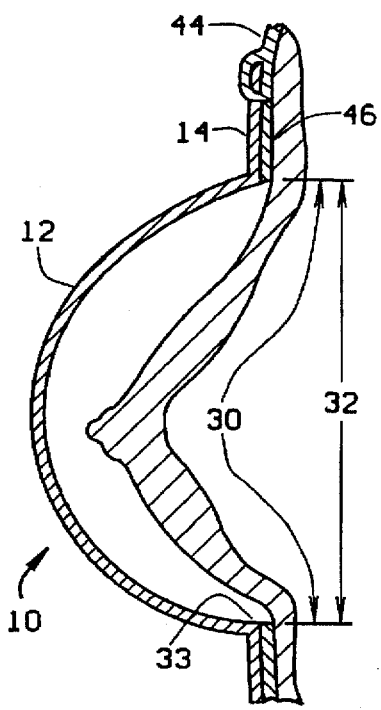
FIG. 2 is a cross-sectional view of the breast enlargement embodiment taken in the plane of line 2—2 of FIG. 1.

One specific embodiment includes a dome 12 configured to fit over a human breast as shown in FIGS. 1 and 2. This embodiment includes a rim 14 having a surface area 34 greater than the normal area 32 of the dome opening thereby preventing medical complications to the soft tissue as long as the pressure is properly regulated within the dome 12. The pressure reducing means 16 is located underneath the patient's breast, so that the apparatus 10 may be hidden under loose-fitting clothes. As with the general embodiment, the vacuum pump assembly 16 of this embodiment is preferably comprised of a vacuum pump 20 with a power source 22, a pressure sensor 24 and servomechanism 26 to drive and control the vacuum pump and to regulate the pressure within the dome 12.

As shown in FIG. 1, this specific embodiment may take the form of a bra 40 having two domes 12 spaced by a hinge 42. Straps 44 may be attached to the bra 40 to retain the bra 40 in place. A gasket 46 may also be included about the rim 14 to improve the patient's comfort and enhance the seal about the rim. In the preferred embodiment, this gasket 46 may be a silicone gel cushion or other soft, conforming type material. Petroleum jelly may also be used to supplement or supplant the gasket. A manual override 48 is included on the vacuum pump assembly 16 so that the patient or doctor may vary the pressure below the optimal level so as to be more comfortable. Although two vacuum pump assembly 16 may be used, one depending from each dome 12 so as to provide different pressures in the domes, the preferred embodiment places the domes in fluid communication with a conduit 50.

Figure 5:
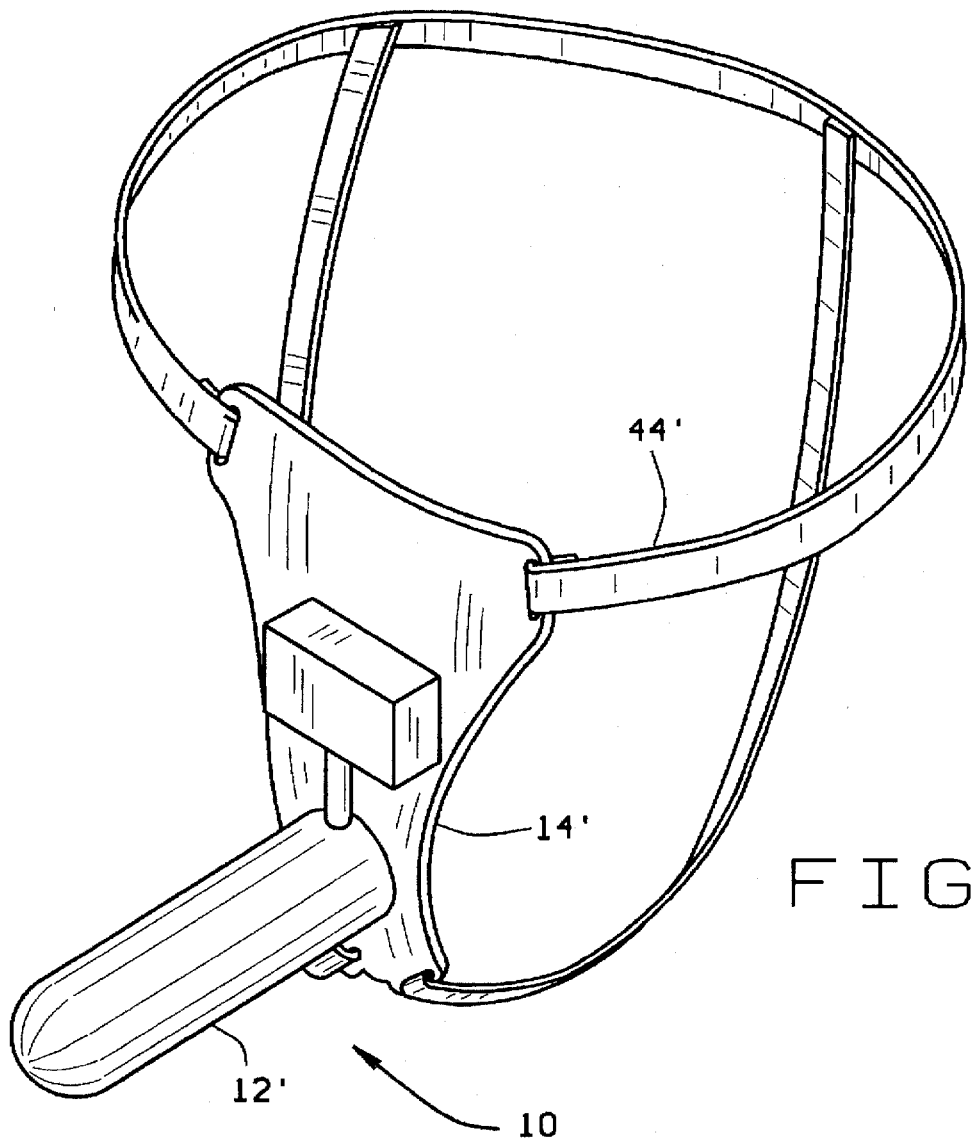
FIG. 5 is an orthographic projection of the penile augmentation embodiment of the present invention.

A second specific embodiment is shown in FIG. 5 wherein the dome 12 is configured to fit over a human penis. As can be seen from the figure, this embodiment comprises essentially the same features as the bra embodiment described above. The principal differences between these embodiments are the configurations of the dome 12' and rim 14' as well as the positioning of the straps 44'.

In order to use the invention, the patient places the dome over the area of desired enlargement and adjusts the straps for comfort. Then the patient simply turns the vacuum pump on and the device goes to work. These apparatuses are intended to be worn 8–12 hours per day and can be worn during sleep. After several months, notable and long-term enlargement should occur. When the desired enlargement is achieved, the use of the device may be suspended. If additional enlargement is desired, then use may be continued. Occasional use or use at a reduced pressure may also be desired to maintain the desired enlargement.

There are various changes and modifications which may be made to the invention as would be apparent to those skilled in the art. However, these changes or modifications are included in the teaching of the disclosure and it is intended that the invention be limited only by the scope of the claims appended hereto.

What is claimed is:

1. An apparatus for enlarging a patient's soft tissue comprising:

a dome for enclosing a portion of the patient's soft tissue desired to be enlarged, said dome having an opening surrounded by a periphery defining a normal area and being sufficiently rigid to withstand a vacuum therein; and a rim adapted to surround said enclosed soft tissue for supporting said dome said rim having a contact surface area sufficiently large to provide a contact pressure less than a pressure which will cause damage to the tissue beneath said rim.

2. The apparatus of claim 1 wherein said dome is sufficiently rigid to withstand 35 mm Hg of negative pressure therewithin.

3. The apparatus of claim 2 further comprising a vacuum pump connected to said dome for reducing the pressure therewithin.

4. The apparatus of claim 3 further comprising a regulator connected to said vacuum pump for maintaining a desired vacuum within said dome.

5. The apparatus of claim 4 further comprising a gasket positioned between said rim and said patient for improved comfort and sealing of said dome.

6. The apparatus of claim 5 further comprising a manual control for said vacuum pump to permit patient adjustment of the vacuum within the dome.

7. The apparatus of claim 4 further comprising:

a second one of said dome and rim combinations;

a hinge joining said rims; and a fluid communication means connected between said domes to thereby equalize the vacuum therein.

8. The apparatus of claim 7 wherein each dome is configured to surround a human breast.

9. The apparatus of claim 4 further comprising:

a second one of said dome and rim combination;

a hinge joining said rims; and a second vacuum pump and regulator connected to said second dome to thereby permit a different vacuum to be induced in each dome.

10. The apparatus of claim 4 wherein said dome is configured to surround a human penis.

11. A method for enlarging a portion of a patient's soft tissue comprising the steps of:

placing a dome over said soft tissue portion;

creating a vacuum within said dome; and supporting said dome with a support sufficiently large to provide a contact pressure less than a pressure which will cause damage to the tissue beneath said support.

12. The method of claim 11 further comprising the step of regulating the vacuum within the dome.

13. The method of claim 12 wherein the step of regulation includes the step of regulating the vacuum to 35 mm Hg or less.

14. The method of claim 11 wherein the step of supporting the dome includes the step of supporting the dome with a rim having a contact surface area substantially equal to or greater than a normal area of said dome defined by a periphery surrounding an opening in said dome.

15. An apparatus for enlarging a patient's soft tissue within the patient's breast, said apparatus comprising:

a pair of domes, each of said pair of domes being configured to surround one of the patient's breasts, each of said pair of domes having an opening surrounded by a periphery defining a normal area and being sufficiently rigid to withstand a vacuum therein; and a pair of rims, each of said pair of rims adapted to surround one of the patient's breasts, each of said pair of rims for supporting one of said pair of domes with a contact surface area sufficiently large to provide a contact pressure less than a pressure which will cause damage to the tissue beneath said pair of rims.

16. The apparatus of claim 15 wherein each of said pair of domes is sufficiently rigid to withstand 35 mm Hg of pressure therewithin.

17. The apparatus of claim 16 further comprising a vacuum pump connected to each of said pair of domes for reducing the pressure therewithin.

18. An apparatus for enlarging a patient's soft tissue comprising means for isolating the soft tissue to be enlarged and means for applying a distracting force within said isolating means and over the isolated soft tissue, wherein said means for isolating includes a rigid, fluid impervious dome adapted to enclose a portion of the patient's soft tissue, said dome having a support sufficiently large to provide a contact pressure less than a pressure which will cause damage to the tissue beneath said dome.

19. The apparatus of claim 18 wherein said force applying means includes a pump for generating a negative pressure.

20. The apparatus of claim 19 wherein said pump has means for applying a constant controlled negative pressure.

21. A method for enlarging a patient's soft tissue, said method comprising the steps of:

isolating a portion of a patient's soft tissue desired to be enlarged with a rigid, fluid impervious dome adapted to enclose the portion of the patient's soft tissue and having a support sufficiently large to provide a contact pressure less than a pressure which will cause damage to the tissue beneath said dome, and applying a distracting force to said isolated soft tissue.

22. The method of claim 21 wherein said force applying step includes the step of applying a negative pressure.

23. The method of claim 21 wherein the force applying step includes the step of applying a constant controlled negative pressure.

24. A portable apparatus for enlarging a patient's soft tissue, said apparatus comprising:

a dome for enclosing a portion of the patient's soft tissue desired to be enlarged, said dome being sufficiently rigid to withstand a vacuum therein; and said dome being adapted to be supported from said patient by a contact surface area sufficiently large to provide a contact pressure less than a pressure which will cause damage to the patient's tissue in contact with said contact surface area.

25. The apparatus of claim 24 further comprising a second dome, each of said domes being adapted to surround one of a woman's breasts.

26. The apparatus of claim 25 wherein said contact surface area substantially surrounds each of said domes.

27. The apparatus of claim 26 further comprising a portable vacuum pump connected to said domes for maintaining a vacuum in said domes.

28. The apparatus of claim 27 further comprising a regulator connected to said portable vacuum pump for regulating the vacuum in said domes.

29. The apparatus of claim 28 wherein said contact surface area includes a gasket substantially surrounding each of said domes.

30. The apparatus of claim 29 wherein said gaskets are made of a soft, conforming material.

31. The apparatus of claim 30 wherein said gaskets are made of silicone gel.

32. The apparatus of claim 30 wherein said vacuum pump includes a pressure sensor for sensing the vacuum in the domes, and a servomechanism for regulating the pressure in said domes.

* * * * *